United States Patent [19]
Neefe

[11] 3,957,049
[45] May 18, 1976

[54] RECHARGEABLE DRUG DELIVERY METHOD

[76] Inventor: Charles W. Neefe, P.O. Drawer 429, Big Spring, Tex. 79720

[22] Filed: May 22, 1975

[21] Appl. No.: 579,796

Related U.S. Application Data

[63] Continuation-in-part of Ser. No. 404,352, Oct. 9, 1973, abandoned.

[52] U.S. Cl. .............................. 128/260; 351/160
[51] Int. Cl.² .......................................... A61M 7/00
[58] Field of Search ........................... 128/260, 268; 260/86.1 R; 351/160, 162

[56] References Cited
UNITED STATES PATENTS

| | | | |
|---|---|---|---|
| 2,241,415 | 5/1941 | Moulton | 351/160 |
| 3,488,111 | 1/1970 | Isen | 351/160 |
| 3,618,604 | 11/1971 | Ness | 128/260 |
| 3,710,796 | 1/1973 | Neefe | 128/260 |
| 3,786,812 | 1/1974 | Neefe | 128/260 |
| 3,870,791 | 3/1975 | Haddad | 424/22 |

Primary Examiner—Aldrich F. Medbery

[57] ABSTRACT

The specification discloses a method of delivering medications at a controlled rate to a selected area of the body, such as to the eye, by the use of a reversible bond between the medication and a receptor for the medication.

4 Claims, 4 Drawing Figures

RECHARGEABLE DRUG DELIVERY METHOD

RELATED APPLICATIONS

This is a continuation-in-part of application Ser. No. 404,352, filed Oct. 9, 1973 entitled DRUG DELIVERY METHOD now abandoned.

FIELD OF THE INVENTION

This invention relates to drug delivery methods, and more particularly relates to a drug delivery method particularly adapted to delivering medication to the eye from a contact lens.

THE PRIOR ART

The delivery of drugs to the cornea at the desired levels over an extended period of time has heretofore been a difficult task. This is due in part to the fact that the cornea has no blood supply, and therefore the circulatory system cannot be relied upon to transport the medications to the cornea. This renders continuous intravenous drip, suppositories, injections and oral administration of drugs of little practical value for delivering medications to the corneal tissues. The use of these delivery methods will in most cases result in a toxic level of the drug in the body fluids beyond the acceptance of the active centers before the effective dosage is reached in the corneal tissue.

Moreover, drops or liquid forms of medication instilled in the eye are quickly diluted by the tears and are rapidly carried away by accelerated lacrimation. The administration of medication orally is unpredictable, as the food and fluid intake of the patient before and after administration can dilute, concentrate, or eliminate the medications at greatly varying rates. Further, injections produce large dosages immediately followed by a steady decrease in the available level of medication.

SUMMARY OF THE INVENTION

In accordance with one embodiment of the present invention, a contact lens having a central optical segment is fabricated to correct any refractive errors the patient may have and therefore provide improved visual acuity while medication is being administered thereby. The medication is contained in the peripheral segment of the lens and is released at a predetermined rate directly to the epithelium of the cornea. As the drug is absorbed into the ocular tissue, the drug will be available at a constant predetermined level.

DESCRIPTION OF THE DRAWINGS

For a more complete understanding of the present invention and for further objects and advantages thereof, reference is now made to the accompanying drawings, in which.

DESCRIPTION OF THE PREFERRED EMBODIMENT

Figure 1:
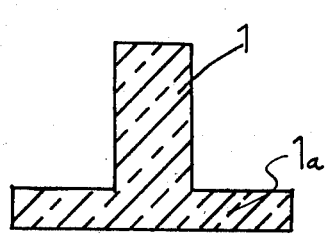
FIG. 1 is a side view of a blank for forming a lens in accordance with the present invention.

FIGS. 1–4 illustrate the formation of a contact lens in accordance with the present invention. Referring to FIG. 1, a cylinder 1 having a diameter of from 2 millimeters to 10 millimeters is formed by any conventional means from a block of transparent water absorbing polymer in the xerogel state. A lower supporting flange 1a is provided at the lower end of the cylinder 1.

Figure 2:
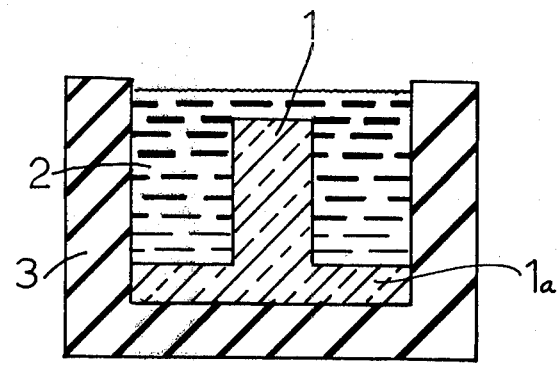
FIG. 2 is a side view of a mold receiving the blank shown in FIG. 1.

Referring to FIG. 2, the cylinder 1 and supporting flange 1a are placed in a suitable mold 3 which may be formed from metal, silicone, rubber or polyethylene. The transparent water absorbing polymer comprising cylinder 1 and supporting flange 1a has a preselected extension when hydrated. Mold 3 is filled with a suitable liquid monomer containing a preselected drug and a suitable catalyst 2. Heat is applied and a liquid monomer 2 is polymerized to form a monolithic mass shown in FIG. 4. The presence of the drug in the outer portion 2 of the mass will render this portion of the mass transparent or opaque, as desired. The central portion 1 of the mass will be transparent.

Figure 3:
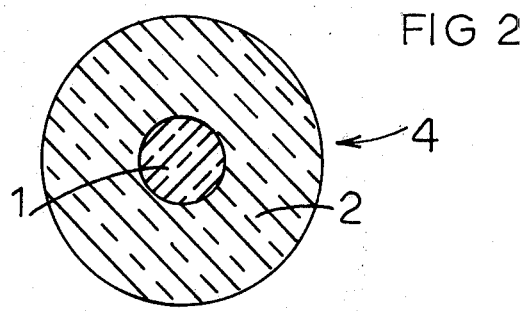
FIG. 3 is a front view of the finished lens in accordance with the invention.
Figure 4:
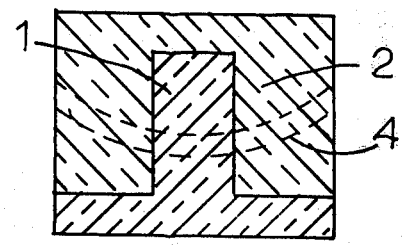
FIG. 4 is a sectional view of the blank from which the lens shown in FIG. 3 is cut.

A lens 4 is cut from the mass shown in FIG. 4 along the dotted line. The front view of the lens 4 is shown in FIG. 3, wherein it may be seen that the lens 4 has a transparent aperture in the center thereof and contains a desired drug medication in the peripheral zone 2. Only the outer peripheral zone 2 will generally be constructed as to enable absorption of an eye drug with a reversible bond. The central segment 1 will generally not be so treated as to absorb eye drugs so as to remain transparent to the eye of the viewer. However, if desired in some cases, the central portion of the lens may also be fabricated to absorb desired quantities of drug in a reversible bond. The expansion of the two materials comprising the center portion 1 and the peripheral zone 2, when hydrated, is generally equal in order to prevent distortion of the lens shape upon hydration.

The release rate of the drug from the peripheral zone 2 may be controlled by a variety of techniques. For example, control of the release rate of the drug may be controlled by varying the solubility of the drug in water, by control of the water content of the lens material or by the permeability of the lens material. Rate of release of the drug may also be provided by microencapsulation of the drug within the lens, or by pre-extraction of the lens. Control of release rate may also be provided with the use of barriers to retard drug migration from the lens, or the drug may alternatively be dispersed within a parsimonious particle to form a matrix in the lens.

The most effective and useful method of controlling release rate is the use of receptor polymer particles containing the drug within the particles. The drug-containing particles are then dispersed within a matrix of drug transporting material within the peripheral zone 2 of lens 4. The receptor polymer has a low water content and may comprise: vinylpyrrolidone 10% to 50%, methyl methacrylate 10% to 40%, ethyleneglycol monomethacrylate 20% to 40%. Cross-linking agents such as allyl methacrylate and ethylene dimethacrylate may be used from 0.1% to 5% to slow the release rate further. An increase in the amount of vinylpyrrolidone also slows the release rate from the particle. Increasing the amount of ethyleneglycol monomethacrylate will increase the rate of drug release from the particle. An example of a drug transporting material suitable for use with the invention is ethyleneglycol monomethacrylate cross-linked with 0.2% ethyleneglycol dimethacrylate when polymerized such that hydrated water soluble drugs may migrate freely through the material.

This method of drug delivery is excellent for the administration of pilocarpine oil or pilocarpine hydrochloride, since a very slow delivery rate is desired over an extended period of time for the control of glaucoma.

Antimicrobial drugs will require a faster release rate, but for a shorter period of time. Examples of useful antimicrobial agents are tetracycline, sulfonamides, ampicillin trihydrate, oxytetracycline, penicillin, chloramphenicol, nystatin and many others. It is understood that each drug may require a different release rate and duration to obtain the desired therapeutic effect.

Another example of a receptor particle and supporting matrix comprises 0.10 grams of pilocarpine oil mixed by ultrasonic energy with 30 grams of vinylpyrrolidone, 20 grams of methyl methacrylate, 48 grams of ethyleneglycol monomethacrylate, 2 grams of ethylene dimethacrylate, and 0.3 grams of tertiary butyl peroctoate. The mixture is placed in an oven at 70°C under a nitrogen atmosphere for five hours to effect polymerization. The resultant friable mass is then reduced to a powder.

The solid receptor particles are dispersed in a partially polymerized liquid comprising 100 grams of ethyleneglycol monomethacrylate, 0.2 grams of ethyleneglycol dimethacrylate and 0.3 grams of tertiary butyl peroctoate. The above mixture is polymerized in a nitrogen atmosphere by heating to 70°C for 5 hours to form the drug transporting matrix.

An important aspect of the invention is that material containing receptor particles made by the above method may be recharged or reactivated after use by immersing the material in a concentrated solution of pilocarpine hydrochloride for eight hours. The use of ultra-sonic energy will increase the absorption of the drug. The desired therapeutic effect can then again be obtained from the recharged lens. The recharged receptor particles retain and slowly release the drug due to the affinity of the receptor particles for the drug molecules when in solution.

The ability to recycle or replenish the medication is of economic importance for many cronic disorders such as glaucoma and diabetes. A drug receptor may be any substance which has an affinity for the drug and concentrates the drug. This ability to recycle is based on a reversible bond between the medication and the receptor material. The effectivity of all drugs depend upon a bond with the biopolymer concerned. The drug delivery bonds are reversible, that is the bond may be easily cleaved. Examples of reversible bonds are ionic, polor, hydrogen, hydrophobic and the von der Waals forces. Covalent bonds in which an electron is shared are irreversible and are not suitable for drug delivery.

The selective bonding of a drug is accomplished by providing receptor sites having moieties of topography which mirror the active sites of the drug molecular topography. The close proximity of the atomic surfaces gives rise to the reversible bonds such as von der Waals forces, hydrogen bond and hydrophobic bonds which provide the means of drug delivery. Since the receptors required may be insoluble in the carrier or may be rendered inactive by the carrier monomers during polymerization the use of a particle containing the receptor in a matrix of drug transporting material is desirable. The particles also provide a large surface area as they may be finely divided and evenly distributed throughout the carrier material.

A detailed description of the drug and receptor active sites and the molecular forces may be found in Andrejus Korolkovas' book, *Essentials of Molecular Pharmocology*, Copyright 1970 by John Wiley & Sons, Inc.

The selective bonding and affinity for the drug in solution results in a concentration of the drug in the receptor media. This affinity may be with the hydrophillic material itself or a receptor embedded within a hydrophillic carrier. The selective bonding and concentration of the drug from the storage solution provides for drug economy and control of release action.

Whereas the present invention has been described for use with a contact lens for administering drugs, it will be understood that the present technique may be utilized for a variety of other types of devices for the administration of drugs over an extended period of time to preselected portions of the body. For example, the technique may be utilized to form a liner for dentures wherein the medical release rate will be increased at mealtime due to the pressure variation imposed by eating. Alternatively, vaginal suppositories may also be made for the material for the control and recyclable administration of drugs, including hormones for birth control. The systemic disturbences will be greatly reduced due to rejection of the required level of medication present in the bloodstream.

Whereas the present invention has been described with respect to specific embodiments thereof, it will be understood that various changes and modifications will be suggested to one skilled in the art, and it is intended to encompass such changes and modifications as fall within the scope of the appended claims.

What is claimed is:

1. A method of delivering a selected drug to a preselected area of a living body comprising the steps of:
   providing a solid receptor chemical compound having an affinity for said selected drug, reducing the solid compound to particles selecting a hydrophillic material permable to the drug when in solution, embedding the particles of said receptor chemical compound in said hydrophillic material,
   attaching said drug to said receptor chemical compound by a reversible bond, and
   reversing said bond to permit release the drug from the receptor chemical compound resulting in said drug going into solution within the permeable hydrophillic material,
   permitting a timed reversal of said bond release to continue until substantially all the solid phase of said material substantially becomes a solution whereby the drug solution may diffuse to the surface of the permeable hydrophillic material and is released to said preselected area of the living body at a preselected rate.

2. The method of claim 1 and further comprising:
   replenishing the quantity of said drug present in the drug depleted receptor chemical compound by immersion of the hydrophillic material in a solution containing said drug.

3. The method of recharging a drug delivery eye contact lens having an outer peripheral segment of a hydrated hydrophillic matrix containing a drug in a reversible bond, said lens further having an unmedicated transparent central optical segment comprising the steps of: removing the lens from the cornea of the eye, immersing the lens in a solution containing a quantity of the drug, permitting the immersed lens to remain in the drug solution until it has absorbed a preselected quantity of the drug within the outer peripheral segment of the lens to recharge the lens, applying the recharged lens to a cornea, and thereby releasing quantities of the drug from the lens to the epithelium of the cornea at a preselected slow delivery rate over an extended period of time.

4. The method of claim 3 and further comprising:

immersing said lens in water to thereby pre-extract excess drug therefrom, and determining the desired effective therapeutic level of drug remaining in the lens by assay of removed drug present in the water to determine the residual drug remaining in the lens.

* * * * *